United States Patent
Whiting

(10) Patent No.: US 7,250,308 B2
(45) Date of Patent: Jul. 31, 2007

(54) CAPTURE ASSAY UTILISING A PARTICULATE ANALYTE

(75) Inventor: Karen Whiting, Cardiff (GB)

(73) Assignee: Genosis (UK) Limited, Surrey (GB)

( * ) Notice: Subject to any disclaimer, the term of this patent is extended or adjusted under 35 U.S.C. 154(b) by 498 days.

(21) Appl. No.: 10/240,652

(22) PCT Filed: Apr. 2, 2001

(86) PCT No.: PCT/GB01/01509

§ 371 (c)(1),
(2), (4) Date: Feb. 3, 2003

(87) PCT Pub. No.: WO01/75434

PCT Pub. Date: Oct. 11, 2001

(65) Prior Publication Data

US 2003/0148384 A1    Aug. 7, 2003

(30) Foreign Application Priority Data

Apr. 3, 2000   (GB) .............................. 0008124.0

(51) Int. Cl.
*G01N 33/538* (2006.01)
(52) U.S. Cl. .................... 436/541; 422/55; 422/58; 422/61; 422/73; 422/101; 435/7.2; 435/7.21; 435/287.1; 435/287.2; 435/287.7; 435/288.4; 435/288.5; 435/805; 435/810; 435/970; 436/514; 436/525; 436/536; 436/810

(58) Field of Classification Search .................. 422/55, 422/58, 61, 73, 101; 435/7.2, 7.21, 287.1, 435/287.2, 287.7, 288.4, 288.5, 805, 810, 435/970; 436/514, 525, 536, 541, 810
See application file for complete search history.

(56) References Cited

U.S. PATENT DOCUMENTS 4,822,565 A * 4/1989 Kohler .......................... 422/57
6,391,654 B1 * 5/2002 Bateman ...................... 436/518

FOREIGN PATENT DOCUMENTS

| EP | 0 143 412 | 2/1992 |
| FR | 2 721 112 | 12/1995 |
| WO | WO8808534 A1 * | 11/1988 |
| WO | 00 20866 | 4/2000 |

* cited by examiner

*Primary Examiner*—Christopher L. Chin
(74) *Attorney, Agent, or Firm*—Wenderoth, Lind & Ponack, L.L.P.

(57) ABSTRACT

Device (1) for assaying a particulate analyte, comprising (a) a receptacle (2) for receiving a suspension (5) of particulate analyte, and containing label (3) for the particulate analyte, and (b) a porous detection material (4) that is permeable to label (3) but is impermeable to particulate analyte, the detection material (4) being arranged within receptacle (2) such that introduction of suspension (5) of particulate analyte into receptacle (2) forms liquid communication between label (3) and detection material (4). After liquid sample (5) is introduced into the receptacle (2), capillary flow through the porous detection material (4) begins. Particulate analyte cannot flow through the detection material (4) and is captured at its surface. Addition of liquid sample (5) also releases the label (3) within the receptacle (2), which is then free to flow through the detection material (4). Label (3) encounters the captured analyte and gives a signal (7). Label is prevented from running ahead of the analyte, resulting in high sensitivity.

27 Claims, 3 Drawing Sheets

CAPTURE ASSAY UTILISING A PARTICULATE ANALYTE

All documents cited herein are incorporated by reference in their entirety.

TECHNICAL FIELD

This invention relates to assay devices for measuring analytes. In particular, it relates to devices which capture analytes mechanically within a porous material, rather than using conventional immuno-capture techniques.

BACKGROUND ART

The format of the standard rapid test lateral flow device has remained unchanged for around ten years. Typically, the device will comprise a nitrocellulose strip. A sample is applied to an application zone, from which it flows by capillary action through a zone containing a visibly-labelled antibody specific for the analyte in question. Free and bound label continue to migrate to a capture zone, where an immobilized antibody specific for the analyte binds the analyte-label complex. Free label (unbound antibody) continues to migrate, leaving an analyte-specific signal in the capture zone. These types of lateral flow devices are disclosed in, for example, EP-A-0284232. Numerous variations of the basic assay have been described, including those in WO92/12428, EP-A-0613005, WO97/06439, and U.S. Pat. No. 5,741,662.

In all cases, however, capture of the analyte-label complex is mediated by an immobilized reagent, which is typically an antibody that is specific for the analyte. This is unsatisfactory in many respects.

Firstly, manufacturing quality control is difficult. The solid phase capture membrane is typically made from nitrocellulose, and antibodies are applied to the membrane directly. Nitrocellulose manufacture is not, however, homogeneous. Quality control of the solid phase antibody is therefore limited to testing a statistical sample of devices from the same, but heterogeneous, batch, and assuming that the whole batch will perform within specific tolerances. It is well known, however, that membranes vary considerably, even within a single batch or lot number.

Secondly, they are relatively cumbersome to manufacture. The application of an immobilized antibody to the strip requires a separate step from the application of the mobile labelled antibody. The capture antibody can be sprayed directly onto the nitrocellulose strip, but the label antibody has to be separately applied to fibrous material which is subsequently attached to the nitrocellulose strip, with an overlap to ensure capillary flow.

Thirdly, the antibody is immobilized by spraying a solution onto a membrane. Some of the antibody does not bind to the membrane strongly, however, and some remains loosely associated with the immobilized antibody. This semi-bound or unbound antibody can become mobile when the solvent front passes over it, resulting in lower binding of label at the detection zone. If the device includes a control line, this will capture the additional label which should have been captured at the detection zone. Tests that rely on a comparison of color intensity between control and detection lines, such as ovulation prediction kits, may therefore give false results. Furthermore, application by spraying inevitably leads to diffusion into the membrane, leading to a more diffuse and less focused detection signal.

Fourthly, the sensitivity of the devices is limited by their format. Analyte and labelled-antibody react as they migrate through the membrane, and flow rates are therefore adjusted to enable the labelled-antibody to flow at the solvent front in order to maximize the amount of time in which the analyte-label complex can form. The complex passes over the capture antibody for a short time, however, thus imposing constraints on the design of the test and its performance characteristics. The short reaction time decreases sensitivity, and also means that high affinity capture antibodies are required.

Finally, the shelf-life of these test devices is often limited by the collapse of the immobilized capture antibody onto the membrane over time.

These shortcomings in the prior art devices are addressed by international patent application WO00/20866, which discloses a device for assaying an analyte, comprising a labelling zone, where a label can bind to the analyte, in communication with a capture zone, wherein the pore size of the capture zone is such that label which is not bound to the analyte can migrate therethrough, whereas label which is bound to the analyte cannot. During migration from the labelling zone to the capture zone, therefore, unbound label can pass into and through the capture zone, whereas bound label will be captured at the junction of the labelling zone and the capture zone.

A similar concept is disclosed in international patent application PCT/GB00/04140, which discloses a lateral flow device for assaying an analyte, having a porous reaction zone in communication with a porous filter zone, wherein the reaction zone contains (i) an analyte-specific label and (ii) a particulate carrier having an analyte-specific capture reagent immobilized thereon. The filter zone has a smaller pore size than that of the reaction zone, such that label that is not bound to the particulate carrier can migrate into the filter zone, whereas label that is bound to the particulate carrier cannot.

The main difference between these two applications is that in WO00/20866, the flow of the analyte is retarded, whereas in PCT/GB00/04140, the flow of the particulate carrier is retarded. In both cases, however, reduced pore size is used for immobilization on the strip, rather than using conventional immuno-capture techniques.

It has now been found that sensitivity of devices that use small pores to capture reagents can be increased by allowing direct contact between the porous capture material and the analyte.

SUMMARY OF THE INVENTION

The invention provides a device for assaying a particulate analyte, comprising (a) a receptacle for receiving a suspension of the particulate analyte, and containing a label for the particulate analyte, and (b) a porous detection material that is permeable to the label but is impermeable to the particulate analyte. The detection material is arranged within the receptacle such that introduction of the suspension of the particulate analyte into the receptacle forms a liquid communication between the label and the detection material.

Compared with the devices of WO00/20866 and PCT/GB00/04140, in which analyte and label interact before meeting the zone with reduced pore size, the device of the present invention can capture the particulate analyte and then allow label to bind to it. This prevents label from running ahead of the analyte, resulting in much better assay sensitivity.

Typically, after a liquid sample is introduced into the receptacle, capillary flow through the porous detection material begins. Particulate analyte cannot enter and flow through the detection material, however, so it is captured at or near its surface. The addition of the liquid sample also releases or activates the label within the receptacle, which is then free to flow into and through the detection material. Label encounters the captured analyte and gives a signal. Surprisingly, the signal is discrete and sharp.

DETAILED DESCRIPTION OF THE INVENTION

The Porous Detection Material

Figure 1:
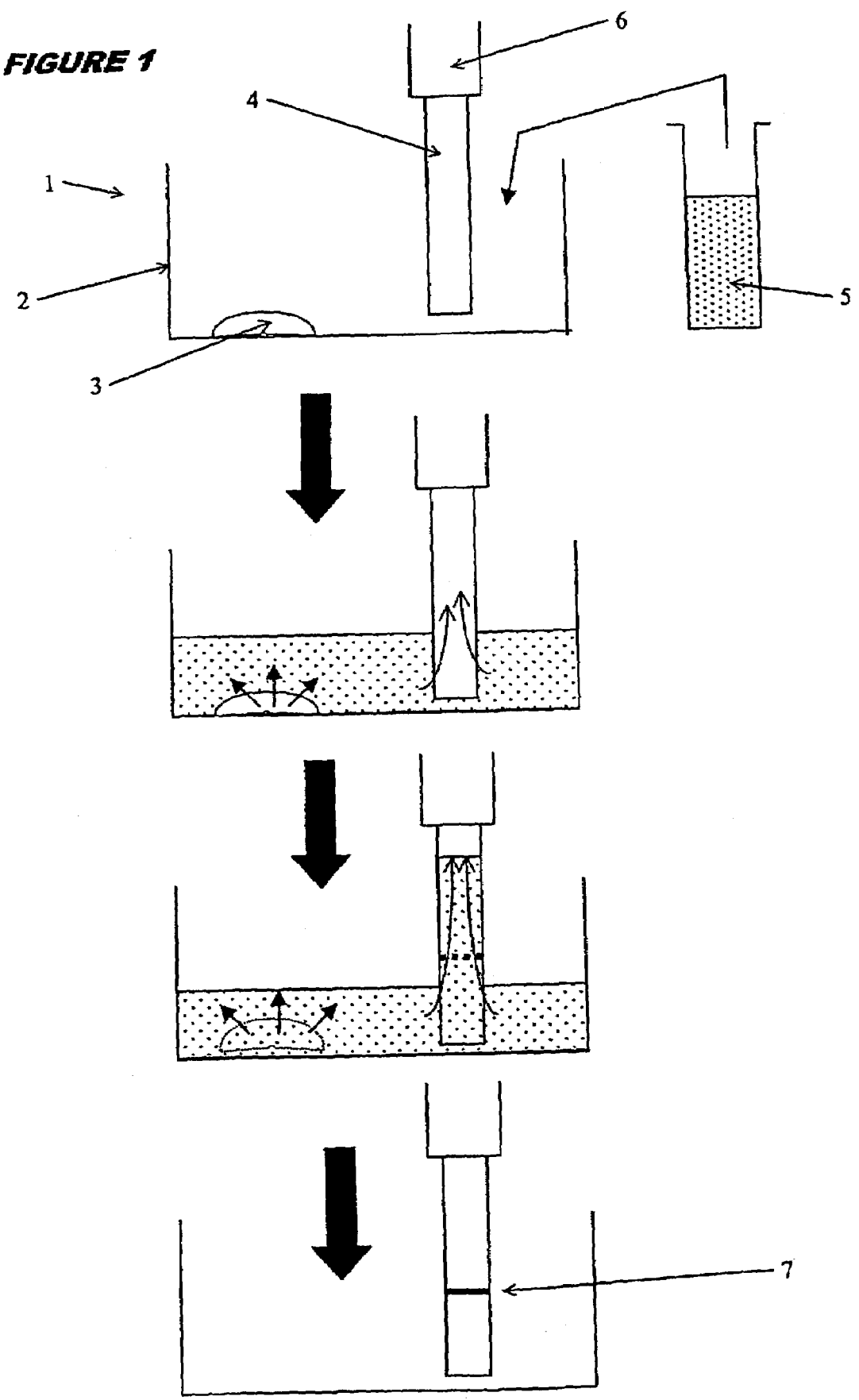
FIG. 1 is a schematic drawing illustrating steps of assaying using the present invention.

The porous detection material is permeable to label but is impermeable to the particulate analyte. This means that particulate analyte cannot enter and flow through it, but is instead captured at or near its surface. Label can flow into and through the detection material, binding to any captured analyte. As the concentration of analyte in a sample increases, the amount of label retained by the detection material also increases, thus allowing semi quantitative measurement of analyte. Significantly, the analyte is not within a fibrous matrix at the point of contact with the porous detection material (i.e., the porous detection material has a pore size that substantially prevents the particulate analyte from entering the detection material at the point where the particulate analyte contacts the detection material).

The detection material can be made from any suitable porous material through which unbound label can migrate whilst particulate analyte cannot. This requirement will be reflected in the pore size of the detection material. In one embodiment, the detection material is made from HDPR with a nominal pore size of between 1–100 µm, preferably between 15–75 µm, and more preferably between 25–50 µm. In another embodiment, the detection material is made from nitrocellulose, with a nominal pore size of between 1–15 µm, preferably between 3–10 µm, and more preferably with a nominal pore size between 5–8 µm (e.g. 6 µm).

As is well known to those in the art, the nominal pore size of a porous material can be determined by hard particle challenge testing (i.e., by determining the maximum diameter of spherical particles which can pass through the material). Alternatively, the pore size of a material may be determined by measuring its 'bubble point'. The bubble point is the pressure required to force air through a (water) wet membrane, and correlates with the pore size as measured by particle retention (although at extremes of pressure and pore size, the correlation may be weaker). The bubble point is generally easier to measure than particle retention and is thus the preferred test when assessing pore size.

When the device of the present invention is to be used for assaying a motile analyte in particular (such as motile spermatozoa or motile bacteria), the appropriate pore size may be determined empirically by routine testing.

The porous detection material is arranged within the receptacle such that introduction of a liquid suspension of analyte into the receptacle forms a communication between the label and the detection material. Before addition of the suspension, the label and the detection material are not in liquid communication, such that label cannot enter the detection material by capillary action. After addition of the suspension, however, the label is activated and can migrate into and through the porous detection material, where it can bind to any captured analyte.

The porous detection material is preferably in the form of a strip.

The Particulate Analyte

The device is particularly suitable for assaying analytes such as biological cells, which are naturally particulate. Preferred cells for assay are mammalian cells and micro-organisms.

The analyte is preferably spermatozoa. The label preferably recognizes a surface antigen which is present on the majority of a population of spermatozoa, rather than a subset. Whilst sperm-specific antigens may be used (e.g. P34H (WO97/40836), SP-10 (WO95/29188), see also EP-A-0387873), 'universal' antigens such as CD59 may be used. It will be appreciated that, where the antigen is not sperm-specific (i.e. it is also present on other cell types, such as CD59), the sample being analyzed may require treatment to remove non-spermatozoa cells. Typically, the sperm-containing sample to be analyzed will not be 'neat' semen, but will be diluted, and possibly treated to remove non-spermatozoa cells. If 'neat' semen is analyzed, it will generally be necessary to use a sperm-specific label, so that non-spermatozoa cells are not labelled. The detection material for retarding the passage of spermatozoa is preferably a nitrocellulose membrane with a nominal pore size of between 5 µm and 8 µm. A sperm sample may be treated to separate motile and non-motile cells before analysis (eg. international patent applications WO99/66331 and WO00/09648). The device of the invention can be used to determine the relative numbers of motile and non-motile cells in a sample by comparing results after such a separation. The device may thus comprise means to separate motile spermatozoa from non-motile spermatozoa before introduction into the receptacle. It is not always necessary to separate cells in this way, however. For example, in vasectomy verification, a test can simply indicate overall levels of spermatozoa, motile or not.

As an alternative, the analyte may be a micro-organism. The micro-organism might be a bacterium, such as enterotoxigenic *E. coli* ('ETEC') [e.g. see Levine (1987) *J. Infect. Dis* 155:377–289], for which any suitably-labelled ETEC-specific antibody can be used as the label, such as gold-conjugated anti-CFA/I monoclonals. The micro-organism might also be a yeast, such as *Candida*.

The particulate analyte typically has a mean diameter of between 0.1 µm and 100 µm. Preferred size ranges for the analyte are 0.1–10 µm and 0.1–1 µm.

Where the analyte is not naturally particulate (e.g. it is soluble), it has to be made into particulate form in order to be assayed by the device of the invention. This will typically be achieved by attaching the analyte to the surface of a small particle e.g. mono-dispersed particles such as beads, liposomes, microparticles, microspheres, aggregates, etc. Preferred small particles are polymeric beads or particles, such as latex or polystyrene beads. The small particle will be coated with a receptor for the analyte, such as an immobilized antibody. The receptor-coated particle is then mixed with a sample such that analyte in the sample can bind to the particle via the receptors. This gives a particle-receptor-analyte complex that is a particulate analyte suitable for assay according to the present invention.

Preferred analytes that can be made into particulate form for assay are hormones, more preferably female hormones related to fertility such as FSH, LH, hCG etc.

The Label

The label is typically an antibody which can bind to the analyte of interest, and which has been suitably tagged. The tag is preferably visible to the naked eye (e.g., a fluorescent or colored tag), and is preferably particulate (e.g. colloidal gold, which is visible as a pink color). It will be appreciated that the term 'antibody' may include polyclonal and monoclonal antibodies, as well as antibody fragments (eg. F(ab)$_2$, Fc etc.), sFv's etc. provided that the necessary biological specificity is retained. As an alternative, the label may be a stain such as eosin.

The label is contained within the receptacle. The label is preferably in dried form, such that it is re-constituted by addition of the liquid sample. Label may be attached to the receptacle (e.g. by spotting the label in liquid form, followed by drying) or may be free within the receptacle (e.g. a pellet of freeze-dried label).

The Device

The device may include a downstream internal reference line comprising a reagent which can immobilize label which was not retained by the detection material. Comparison of the amount of label bound by the detection material with the amount bound by the reference line allows semi-quantitative or quantitative results to be measured.

The device of the invention can be produced simply and cheaply, conveniently in the form of a test strip or dipstick. Furthermore, it can be used very easily, for instance by the home user. The invention thus provides an assay device which can be used at home as a basic screen of, for instance, male fertility.

By appropriately employing particulate antibody or antigen and labelled binding partner, it will be appreciated that the device may be adapted to a competitive format, as is known in the art.

The invention also provides a kit comprising (a) a receptacle containing a label and (b) a porous detection material. The kit may be used to assemble a device of the invention, or may be used by adding sample to the receptacle, thereby activating the label, and then inserting the detection material into the sample/label mixture.

Processes

The invention provides a process for assaying a particulate analyte, comprising the steps of:

providing a receptacle that contains (i) a label for the particulate analyte and (ii) a porous detection material that is permeable to the label but is impermeable to the particulate analyte, the detection material and the label not being in liquid communication;

adding a suspension of the particulate analyte to the receptacle, thereby creating a liquid communication between the detection material and the label;

allowing liquid in the suspension to flow into the detection material such that the particulate analyte is captured by the detection material; and detecting the interaction between the label and the captured analyte.

Where the analyte is not naturally particulate, the process preferably comprises the initial steps of mixing the non-particulate analyte with a particle that is coated with a receptor for the analyte, in order to form a particle-receptor-analyte complex.

EXAMPLE 1

A semen sample was separated using sodium hyaluronate at 0.88 mg/ml (Anika, Woburn, Mass.) diluted in Earle's Balanced Salt solution (Gibco BRL, Life Technologies, Scotland) containing 0.45% Bovine serum albumin (Intergen, N.Y.) and 10 mM HEPES buffer (Sigma, St. Louis, Mo.).

The number of sperm in the separated sample was counted as 30 million per ml. Aliquots were taken and serially diluted in EBSS to give five samples containing 30, 15, 7.5, 3.75 and 1.9 million sperm per ml.

The assaying device (1) shown in FIG. 1 comprises a plastic receptacle (2). The bottom of the receptacle (2) has a small patch of precipitated label (3), comprising monoclonal anti-CD59 labelling antibody conjugated to 40 nm gold OD 10.0 (BRIC 229 clone, IGBRL, Bristol, UK). Within receptacle (2) is a 1 cm strip of SRHF nitrocellulose (porous strip) (4) (Millipore Corporation, Bedford, Mass.; high flow membrane SPHF04020), to which is attached a 3 cm wick (6) of absorbent chromatography paper (Whatman, Maidstone, UK).

50 µl of each of the five samples (5) was added to receptacle (2) together with 7.5 µl running buffer (0.5% Triton X-100+5% glucose dissolved in water). The liquid in samples (5) began to migrate through material (4) by capillary action. At the same time, label (3) was re-constituted.

Whilst the liquid in sample (5) can enter material (4) and flow through it, the spermatozoa in the sample are too large. Rather than enter the material (4), their progress is retarded to form a zone (7) of immobilized spermatozoa. After a short period, the re-constituted gold-labelled antibody (3) begins to migrate through material (4), passing and visibly labelling zone (7).

An easily visible signal at zone (7) was observed within 20 minutes for the sample containing 3.75 million sperm per ml.

EXAMPLE 2

Figure 2:
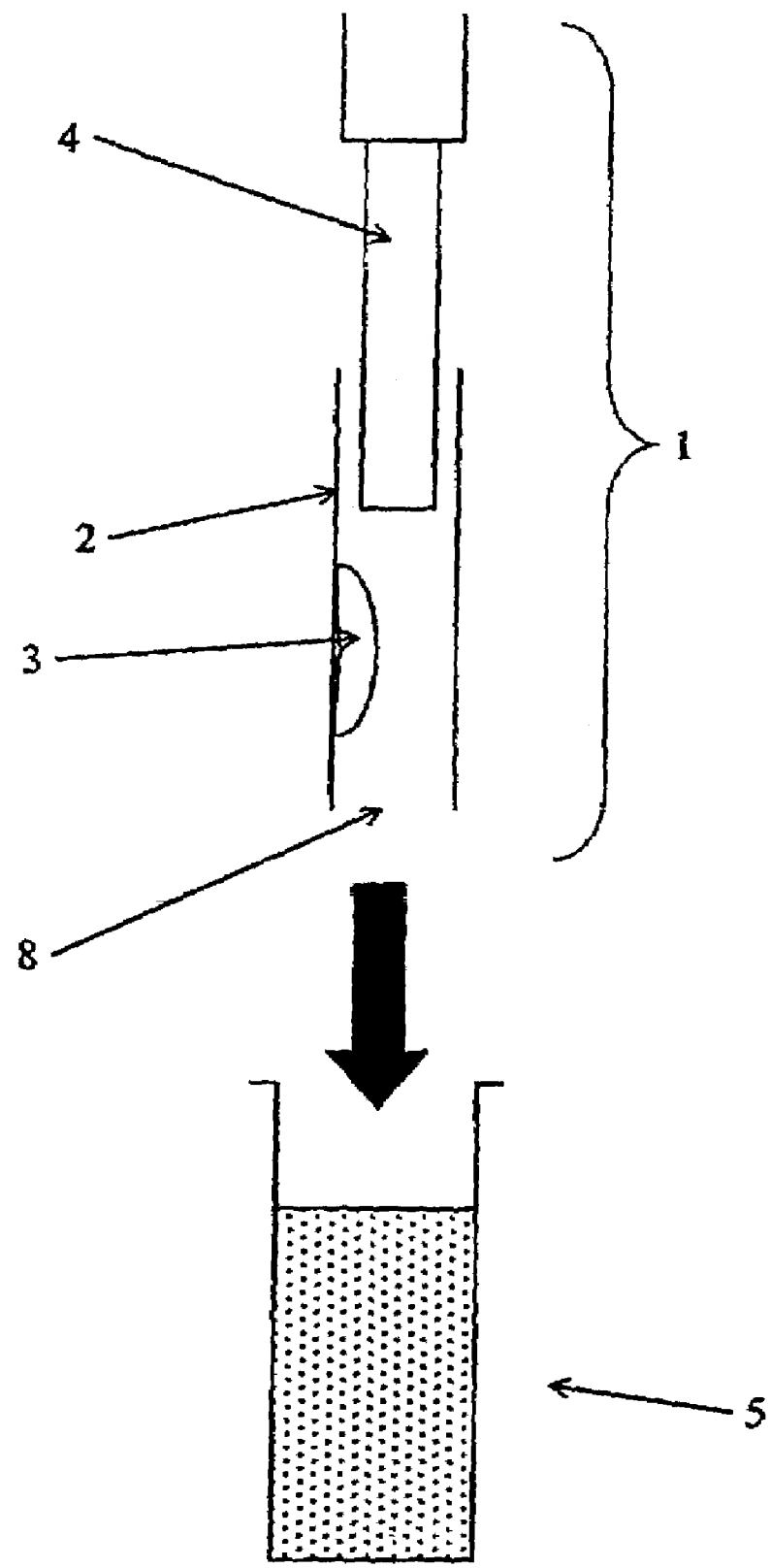
FIG. 2 is a schematic drawing illustrating alternative steps of assaying using the present invention.

As an alternative to the device of example 1, the device illustrated in FIG. 2 was assembled. This receptacle (2) of the device has an open end (8) remote from porous strip (4) and can thus be inserted into a sample (5).

To make receptacle (2), two acetate sheets were placed next to each other. These were placed around strip (4), but close enough to each other to allow capillary flow to occur between them. On one of the sheets, 7.5 l of gold-labelled anti-CD59 was spotted and dried at 37° C. for 1 hour to form label (3). The sides of the receptacle were sealed with sellotape™.

This device was dipped into samples (5) as assayed in example 1. Conjugated antibody was rapidly re-hydrated from the acetate (2–3 minutes) and signal was visible at the interface between the acetate and nitrocellulose membrane at 7.5 million sperm per ml.

EXAMPLE 3

The device of example 1 was adapted to include gold-labelled anti-hCG in patch (3).

Polystyrene particles (Sigma, LB30), 3 µm diameter, were diluted from 10% to 1% solids in borate buffer (pH 8.5, 10 mM). The particles were washed by centrifugation at 3000 rpm for 5 minutes and the supernatant was replaced by an equal volume of fresh borate buffer.

Monoclonal anti-hCG at 5 mg/ml was added to the latex particles to give a final concentration of 150 µg/ml. The suspension was mixed for 1 hour at 20° C. before the addition of BSA to a concentration of 0.02% (w/v). The suspension was mixed for a further 30 minutes at 20° C.

The suspension was centrifuged at 300 rpm for 5 minutes and the supernatant discarded. The pellet was re-suspended in borate buffer (pH 8.5, 10 mM) to give a concentration of 1% (w/v), then washed twice, and each time re-suspended to 1% solids in borate buffer (pH 8.5, 10 mM).

A female urine sample (containing hCG) was mixed with the antibody-conjugated particles to give a sample (5) of particulate hCG analyte. This was added to device (1) and, after re-constitution of label (3) and capillary migration through detection material (4), a pink line (7) was visible.

EXAMPLE 4

Figure 3:
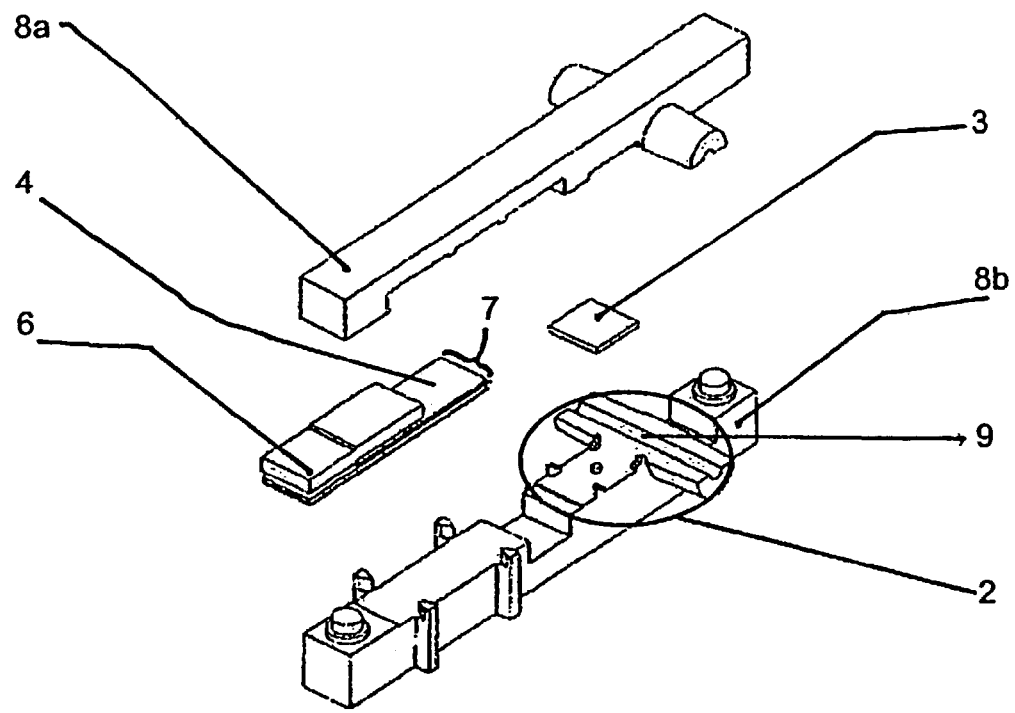
FIG. 3 is an exploded perspective view of a device for performing assaying according to the present invention.
Figure 4:
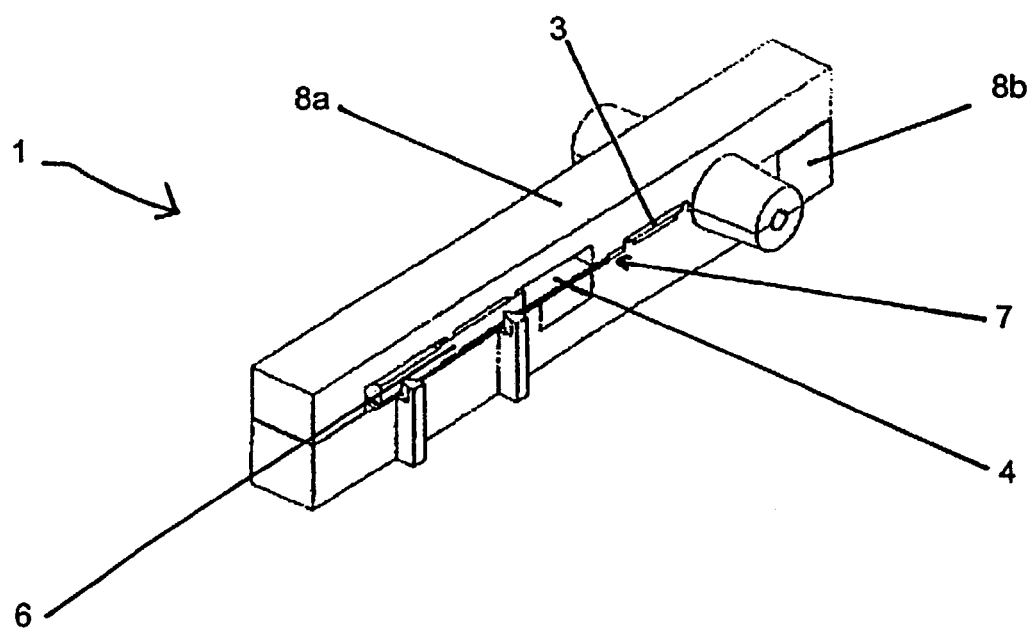
FIG. 4 is a perspective view of the device of FIG. 3.

The device illustrated in FIGS. 3 and 4 was assembled. In the assembled device (1), tubular portion (9) receives a sample containing a particulate analyte (e.g. a sample of motile spermatozoa). Tubular portion (9) may initially be closed (e.g., it may be filled with a plunger which, when withdrawn, fills tubular portion (9) in the manner of a syringe). Liquid flows through tube (9) into the capillary space (2) between clear plastic housings (8a; 8b) and passes under a pad (3) containing dehydrated gold-tagged murine anti-CD59. As liquid passes pad (3), the antibody is re-hydrated and can pass into the liquid, where it is able to bind to spermatozoa. The liquid continues to flow towards and into nitrocellulose (porous strip) strip (4), aided by a wick (6). The pore size of strip (4) is too small to allow the spermatozoa to enter, so they are captured at its entrance (7). Antibody can bind captured spermatozoa at entrance (7) and form a pink line.

FURTHER EMBODIMENTS

It will be understood that the invention is described above by way of example only and modifications may be made whilst remaining within the scope and spirit of the invention.

The invention claimed is:

1. A device for assaying a particulate analyte, comprising:
a receptacle for receiving a suspension of the particulate analyte, said receptacle containing a label for binding to the particulate analyte; and
a porous detection material having a pore size permeable to the label and impermeable to the particulate analyte so as to substantially prevent the particulate analyte from entering into and flowing through said porous detection material, said detection material being arranged within said receptacle to allow, when the suspension is introduced into said receptacle, liquid in the suspension to flow into and through said detection material so as to capture the particulate analyte and allow the label and the particulate analyte to interact such that the label is bound to the particulate analyte.

2. The device of claim 1, wherein said detection material has a nominal pore size in a range of 20 µm to 35 µm.

3. The device of claim 2, wherein said label comprises an antibody.

4. The device of claim 2, wherein said label is tagged with colloidal gold.

5. The device of claim 1, wherein said detection material has a nominal pore size in a range of 5 µm to 8 µm.

6. The device of claim 5, wherein said detection material comprises nitrocellulose.

7. The device of claim 6, wherein said device is operable to assay a biological cell.

8. The device of claim 6, wherein said label comprises an antibody.

9. The device of claim 6, wherein said label is tagged with colloidal gold.

10. The device of claim 5, wherein said device is operable to assay a biological cell.

11. The device of claim 10, wherein said device is operable to assay spermatozoa.

12. The device of claim 11, wherein said label is operable to recognize CD59.

13. The device of claim 12, wherein said label comprises an antibody.

14. The device of claim 12, wherein said label is tagged with colloidal gold.

15. The device of claim 11, wherein said label comprises an antibody.

16. The device of claim 11, wherein said label is tagged with colloidal gold.

17. The device of claim 10, wherein said label comprises an antibody.

18. The device of claim 10, wherein said label is tagged with colloidal gold.

19. The device of claim 5, wherein said label comprises an antibody.

20. The device of claim 5, wherein said label is tagged with colloidal gold.

21. The device of claim 1, wherein said label comprises an antibody.

22. The device of claim 21, wherein said label is tagged with colloidal gold.

23. The device of claim 1, wherein said label is tagged with colloidal gold.

24. The device of claim 1, wherein said detection material has a fibrous matrix at a location whereat the particulate analyte is to contact said detection material, said fibrous matrix having a structure for substantially preventing the particulate analyte from entering therein.

25. A process of assaying a particulate analyte, comprising:
providing a receptacle containing:
a label for binding to the particulate analyte; and
a porous detection material having a pore size permeable to the label and impermeable to the particulate analyte so as to substantially prevent the particulate analyte from entering into and flowing through the porous detection material, the detection material and the label not being in liquid communication;
adding a suspension of the particulate analyte to the receptacle, thereby creating liquid communication between the detection material and the label;
allowing liquid in the suspension to flow into and through the detection material such that the particulate analyte is captured by the detection material, thereby allowing the label to interact with the particulate analyte by binding to the particulate analyte; and
detecting the label bound to the particulate analyte due to the interaction between the label and the captured particulate analyte, thereby indicating the presence of the particulate analyte.

26. The process of claim 25, wherein the detection material has a fibrous matrix at a location whereat the particulate analyte is to contact the detection material, the fibrous matrix having a structure for substantially preventing the particulate analyte from entering therein.

27. The process of claim 26, wherein the particulate analyte is mechanically captured by being collected at a surface of the fibrous matrix.

* * * * *